United States Patent [19]

Chang

[11] 4,039,600
[45] Aug. 2, 1977

[54] CONVERSION OF SYNTHESIS GAS TO AROMATIC HYDROCARBONS

[75] Inventor: Clarence D. Chang, Princeton, N.J.

[73] Assignee: Mobil Oil Corporation, New York, N.Y.

[21] Appl. No.: 592,565

[22] Filed: July 2, 1975

[51] Int. Cl.$^2$ .............................................. B07C 15/00
[52] U.S. Cl. .............................. 260/668 R; 260/449.5
[58] Field of Search ........................ 260/668 R, 449.5

[56] References Cited

U.S. PATENT DOCUMENTS

| | | | |
|---|---|---|---|
| 3,709,919 | 1/1973 | Magoon | 260/449.5 |
| 3,745,108 | 7/1973 | Schuman | 208/8 |
| 3,839,186 | 10/1974 | Berger | 208/8 |
| 3,894,107 | 7/1975 | Butter et al. | 260/668 R |
| 3,907,915 | 9/1975 | Chang et al. | 260/668 R |

OTHER PUBLICATIONS

James F. Roth et al. Chem. Tech., vol. 1, pp. 600–605, 1971.

*Primary Examiner*—Veronica O'Keefe
*Attorney, Agent, or Firm*—C. A. Huggett; M. G. Gilman

[57] ABSTRACT

Synthesis gas, a mixture comprising carbon monoxide and hydrogen, is converted to a product comprising methanol and unreacted carbon monoxide, possibly with hydrogen; the mixture is partially converted by carbonylation to a mixture comprising acetic acid, methanol and methyl acetate; and this mixture is converted to a hydrocarbon product rich in aromatic hydrocarbons by use of a high silica to alumina ratio, limited constraint index, zeolite such as a ZSM-5 zeolite.

8 Claims, No Drawings

CONVERSION OF SYNTHESIS GAS TO AROMATIC HYDROCARBONS

This invention is directed to the conversion of non-petroleum fossil fuel, and such as natural gas or coal, to light hydrocarbon gases and gasoline boiling range aromatic hydrocarbons. It more particularly refers to such as process having an improved yield of such aromatic hydrocarbons at the expense of such light hydrocarbon gases.

It is known, from other patents and patent applications of the instant inventors, some of them and/or coworkers, that there has recently been discovered a new and most efficient technique for converting various lower organic compounds containing oxygen, sulfur or halogen hetero atoms to higher aromatic compounds. In particular, these other patents and/or patent applications have disclosed that alcohols, ethers, carbonyls and/or their sulfur and halogen analogs are readily converted to mixtures of hydrocarbons covering the full range from $C_1$ to about $C_{10}$ by relatively high temperature contact with a special zeolite as described below. This conversion has been disclosed to be useful at about 500° to 1200° F and space velocities of about 0.1 to 50 LHSV. Higher space velocities have also been found to be useful, particularly if less than complete conversion and/or more highly olefinic product is desired.

There have also been disclosed, in similarly related patents and patent applications, various techniques for taking advantage of this remarkable new conversion process in order to be able to ultimately convert coal or natural gas to high octane gasoline via synthesis gas production, methanol synthesis and methanol conversion to aromatics via the above described novel synthesis. Even more recently, further advances in this technology have permitted remarkable improvements in direct conversion of synthesis gas to complex hydrocarbons in a single stage over a particular group of composite catalysts which may utilize as the zeolite component a special high silica to alumina ratio zeolite as described below.

The special zeolite catalysts referred to herein utilize members of a special class of zeolites exhibiting some unusual properties. These zeolites induce profound transformations of aliphatic hydrocarbons to aromatic hydrocarbons in commercially desirable yields and are generally highly effective in alkylation, isomerization, disproportionation and other reactions involving aromatic hydrocarbons. Although they have unusually low alumina contents, i.e., high silica to alumina ratios, they are very active even with silica to alumina ratios exceeding 30. This activity is surprising since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g. of the X and A type. Furthermore, carbonaceous deposits, when formed, may be removed by burning at higher than usual temperatures to restore activity. In many environments, the zeolites of this class exhibit very low coke forming capability, conducive to very long times on stream between burning regenerations.

An important characteristic of the crystal structure of this class of zeolites is that it provides constrained access to, and egress from, the intra-crystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful as catalysts in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The zeolites useful as catalysts in this invention freely sorb normal hexane and have a pore dimension greater than about 5 Angstroms. In addition, their structure must provide constrained access to some larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is substantially excluded and the zeolite is not of the desired type. Zeolite with windows of 10-membered rings are preferred, although excessive puckering or pore blockage may render these zeolites substantially ineffective. Zeolites with windows or 12-membered rings do not generally appear to offer sufficient constraint to produce the advantageous conversions desired in the instant invention, although structures can be conceived, due to pore blockage or other cause, that may be operative.

Rather than attempt to judge from crystal structure whether or not a zeolite possesses the necessary constrained access, a simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F for at least 15 minutes. The zeolite is then flushed with helium and the temperature adjusted between 550° and 950° F to give an overall conversion between 10 and 60%. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The constraint index is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those which employ a zeolite having a constraint index from 1.0 to 12.0. Constraint Index (CI) values for some typical zeolites including some not within the scope of this invention are:

| CAS | C.I. |
| --- | --- |
| ZSM-5 | 8.3 |
| ZSM-11 | 8.7 |
| ZSM-35 | 4.5 |
| TMA Offretite | 3.7 |
| ZSM-12 | 2 |
| ZSM-38 | 2 |
| Beta | 0.6 |
| ZSM-4 | 0.5 |
| Acid Mordenite | 0.5 |
| REY | 0.4 |
| Amorphous Silica-alumina | 0.6 |
| Erionite | 38 |

The above-described Constraint Index is an important and even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint Index seems to vary somewhat with severity of operation (conversion). Therefore, it will be appreciated that it may be possible to so select test conditions to establish multiple constraint indexes for a particular given zeolite which may be both inside and outside the above defined range of 1 to 12.

Thus, it should be understood that the Constraint Index value as used herein is an inclusive rather than an exclusive value. That is, a zeolite when tested by any combination of conditions within the testing definition set forth herein above to have a constraint index of 1 to 12 is intended to be included in the instant catalyst definition regardless that the same identical zeolite tested under other defined conditions may give a constraint index value outside of 1 to 12.

The class of zeolites defined herein is exemplified by ZSM-5, ZSM-11, ZSM-12, ZSM-21, ZSM-35, ZSM-38 and other similar material. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

U.S. patent application Ser. No. 358,192, filed May 7, 1973, the entire contents of which are incorporated herein by reference, describes a zeolite composition, and a method of making such, designated as ZSM-21 which is useful in this invention.

U.S. patent application Ser. No. 528,061 filed Nov. 29, 1974, the entire contents of which are incorporated herein by reference, describes a zeolite composition including a method of making it. This composition is designated ZSM-35 and is useful in this invention.

U.S. patent application Ser. No. 528,060, filed Nov. 29, 1974, the entire contents of which are incorporated herein by reference, describes a zeolite composition including a method of making it. This composition is designated ZSM-38 and is useful in this invention.

The x-ray diffraction pattern of ZSM-21 appears to be generic to that of ZSM-35 and ZSM-38. Either or all of these zeolites is considered to be within the scope of this invention.

The specific zeolites described, when prepared in the presence of organic cations, are substantially catalytically inactive, possibly because the intracrystalline free space is occupied by organic cations from the forming solution. They may be activated by heating in an inert atmosphere at 1000° F for 1 hour, for example, followed by base exchange with ammonium salts followed by calcination at 1000° F in air. The presence of organic cations in the forming solution may not be absolutely essential to the formation of this special type zeolite; however, the presence of these cations does appear to favor the formation of this special type of zeolite. More generally, it is desirable to activate this type zeolite by base exchange with ammonium salts followed by calcination in air at about 1000° F for from about 15 minutes to about 24 hours.

Natural zeolites may sometimes be converted to this type zeolite by various activation procedures and other treatments such a base exchange, steaming, alumina extraction and calcination, alone or in combination. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12 and ZSM-21, with ZSM-5 particularly preferred.

The zeolites used as catalysts in this invention may be in the hydrogen form or they may be based exchanged or impregnated to contain ammonium or a metal cation complement. It is desirable to calcine the zeolite after base exchange. The metal cations that may be present include any of the cations of the metals of Groups I through VIII of the periodic table. However, in the case of Group IA metals, the cation content should in no case be so large as to substantially eliminate the activity of the zeolite for the catalysis being employed in the instant invention. For example, a completely sodium exchange H-ZSM-5 appears to be largely inactive for shape selective conversions required in the present invention.

In a preferred aspect of this invention, the zeolites useful as catalysts herein are selected as those having a crystal framework density, in the dry hydrogen form, of not substantially below about 1.6 grams per cubic centimeter. It has been found that zeolites which satisfy all three of these criteria are most desired. Therefore, the preferred catalysts of this invention are those comprising zeolites having a constraint index as defined above of about 1 to 12, silica to alumina ratio of at least about 12 and a dried crystal density of not substantially less than about 1.6 grams per cubic centimeter. The dry density for known structures may be calculated from the number of silicon plus aluminum atoms per 1000 cubic Angstroms, as given, e.g. on page 19 of the article on Zeolite Structure by W. M. Meier. This paper, the entire contents of which are incorporated herein by reference, is included in "Proceedings of the Conference or Molecular Sieves, London, April, 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, seems to be important as the locus of catalytic activity.

Crystal framework densities of some typical zeolites including some which are not within the preview of this invention are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

Since the conversion of non-petroleum fossil fuels, such as coal and/or natural gas, to high quality hydrocarbon gasoline and/or to high quality petrochemical feed stocks is a most desirable accomplishment, it is an important object of this invention to provide an improved process for accomplishing this result.

Another important object of this invention is to provide a novel combination of unit processes for converting synthesis gas to a product comprising high proportions of aromatic hydrocarbons.

Other and additional objects of this invention will become apparent from a consideration of this entire specification including the claims and drawing hereof.

In accord with and fulfilling these objects, one aspect of this invention resides in a specific improvement in the previously described conversion of synthesis gas to hydrocarbon gasoline via methanol synthesis.

It is usual industrial practice to carry out commercial methanol synthesis reactions to about 15 to 20 percent conversion, separate the unreacted carbon monoxide and hydrogen from the produced methanol, and recycle the unreacted reactants to produce further quantities of methanol. In the prior disclosed gasoline producing processes, this methanol is then separately converted to gasoline.

According to the instant invention, the methanol synthesis product comprising methanol admixed with unreacted carbon monoxide is not resolved to recover the methanol therefrom, as in the referred to prior patent applications, but rather is, in admixture, contacted with a carbonylation reaction catalyst at carbonylation temperatures in order to react some of the methanol with the unreacted carbon monoxide to produce a product comprising a mixture of methanol, acetic acid and methyl acetate. This mixture is then converted to a complete mixture of hydrocarbons including $C_6$ to $C_{10}$ monocyclic aromatic hydrocarbons by contact, under conversion conditions, with a special zeolite as abovedescribed.

It has been discovered, and it is a most important feature of this invention, that the conversion of carbon in the carbon monoxide reactant to carbon in the $C_6$ to $C_{10}$ monocyclic aromatic hydrocarbon products is increased by operating according to this invention with an intermediate additional carbonylation step as compared to recycling the carbon monoxide to extinction to methanol synthesis as previously proposed. It has previously been disclosed that all of the components of the efflux of the carbonylation reaction are individually convertible over the above described special zeolite catalyst to high quality hydrocarbon gasoline. This previous disclosure would necessarily indicate that a mixture of these individual components should be similarly convertible over this catalyst to these products. The instant invention is based part upon the discovery that the particular admixture produced by the combination of methanol synthesis followed by carbonylation, to convert further portions of the fed carbon monoxide to lower organic oxygenate compounds, is convertible to a product having a disproportionate and unexpectedly higher proportion of such aromatic hydrocarbons than one would predict from a consideration of the conversion yields obtainable from individual reactants.

It should be noted that the individual unit processes of the process combination set forth herein are not here considered to be per se novel and inventive. Each of them operates in the manner, with the catalysts, and under the conditions ascribed to them by the appropriate prior art. One novel feature disclosed here is the nature of the feed to the special zeolite conversion. This conversion of this particular feed is believed not to have been elsewhere or prior disclosed.

Production of synthesis gas comprising carbon monoxide and hydrogen from coal and/or natural gas or other feed stocks is quite well known, widely documented and, in some parts of the world, commercially practiced. Adjustment of the relative proportions of the two main constituents, along with that of carbon dioxide and water, is conventional technology. Coal gasification to synthesis gas is generally carried out with oxygen and/or steam at about 1000° to 2000° F, while conversion of natural gas is carried out at about 1000° to 1600° F.

The conversion of synthesis gas to a product comprising methanol is well known commerical technology. This reaction, called methanol synthesis, is carried out at about 450° to 750° F and 600 to 6000 psig using a catalyst comprising zinc and/or copper.

The reaction of methanol with carbon monoxide to produce acetic acid is per se known. It is carried out at about 300° to 800° F and about 15 to 1000 psig. Acidic catalysts such as phosphoric acid or boron trifluoride have been used as have rhodium salts in heterogenous or homogeneous form with an iodine promotor.

The conversions of methanol, acetic acid, methyl acetate or dimethyl ether are per se known to be accomplished at about 500° to 1200° F using a special zeolite catalyst as described above.

According to this invention the purpose of the carbonylation process is to bind more carbon monoxide into the organic product, as methyl formate, acetic acid, methyl acetate or other lower organic oxygenates. Contrary to the desiderata of the established carbonylation art, it is not important how much acetic acid is made or how pure it is, but rather, how much total carbon of the feed synthesis gas has been bound into organic products. It is preferred that the mole ratio of methanol to acetic acid be maintained at at least 12 in the carbonylation product.

It is interesting to note that the description of one commercial operation utilizing a rhodium catalyzed carbonylation of methanol to produce acetic acid which appeared in the October 1971 issue of Chemical Technology showed the use of hydro-iodic acid as a promotor to convert methanol reactant to methyl iodide which is proposed to be the true reactant. In the event that a halogen moiety is used as a promotor as proposed, methyl halide intermediate should be understood to be readily convertible over the special zeolite catalyst hereof to aromatic hydrocarbons. Thus, the yield of desirable $C_6$–$C_{10}$ more cyclic aromatics will be further enhanced even if some of this promotor remains with the acetic acid containing carbonylation product when such is fed to special zeolite conversion.

Comparison of the conversion of carbon monoxide to $C_6$ to $C_{10}$ monocyclic aromatic hydrocarbons via methanol synthesis and special zeolite conversion based upon recycling unreacted carbon monoxide to methanol synthesis and based upon a carbonylation unit process as described herein shows a remarkable advantage for the latter processing configuration. Carbon efficiency to such aromatics is increased from about 30 to about 80% by the practice of this invention.

It is an attribute of this invention that the product ultimately produced upon conversion with the special aromatizing zeolite catalyst described above comprises water and a full range of $C_1$ to about $C_{11}$ hydrocarbons. It is common for this product to be a stoichiometric partition of oxygen and carbon in the feed, that is, substantially all of the oxygen in the organic portions of the feed is converted to water and substantially all of the carbon in the organic portions of the feed is converted to hydrocarbons. Some small amount of carbon oxides may be formed but these are in impurity concentrations. If conversion of the organic feed is less than 100%, the partition of carbon and oxygen seems to be substantially proportional. Of the hydrocarbon product, the major portion is the $C_5+$ normally liquid fractions and the minor portions is the $C_4-$ normally gaseous fractions. Of the $C_5+$ fractions, the major proportion is monocyclic aromatic hydrocarbons, $C_6$ to $C_{10}$. It is possible to increase the olefinicity of the product at the expense of aromatics by increasing space velocity or other means disclosed and claimed elsewhere. In this latter situation, where a highly olefinic product is desired, it is preferred to operate at the higher proportions of methanol to acetic acid. Alternatively, lower proportions of methanol to acetic acid seem to favor production of aromatics.
the olefinicity of the product at the expense of aromatics by increasing space velocity or other means disclosed and claimed elsewhere. In this latter situation, where a highly olefinic product is desired, it is preferred to operate at the higher proportions of methanol to acetic acid. Alternatively, lower proportions of methanol to acetic acid seem to favor production of aromatics.

What is claimed is:

1. A process of converting carbon monoxide to gasoline boiling range aromatic hydrocarbons comprising:
    A. reacting carbon monoxide and hydrogen at about 450° to 750° F in contact with a methanol synthesis catalyst to produce a product comprising methanol and carbon monoxide;
    B. reacting said methanol and said carbon monoxide at about 300° to 800° F in contact with a carbonylation catalyst to produce a product comprising methanol and acetic acid; and
    C. converting said methanol and said acetic acid at about 500° to 1200° F in contact with an aromatizing catalyst comprising a zeolite having a silica to alumina ratio of at least 12 and a constraint index of 1 to 12 to produce a product comprising normally liquid hydrocarbons the major portion of which are a conjunct mixture of $C_6$ and $C_{10}$ mono-cyclic aromatics.

2. The process claimed in claim 1 wherein said methanol synthesis catalyst comprises zinc and copper; said carbonylation catalyst comprises rhodium and said aromatization catalyst comprises a ZSM-5 zeolite.

3. The process claimed in claim 1 including utilizing a homogeneous catalyst comprising rhodium in said carbonylation.

4. The process claimed in claim 1 including recovering carbon monoxide from the product of step C and recycling such to step A.

5. The process claimed in claim 1 including converting a non-petroleum fossil fuel to said carbon monoxide and hydrogen fed to step A.

6. The process claimed in claim 5 including producing a $C_4-$ hydrocarbon gas in step C; separating said gas from said normally liquid hydrocarbon products, and converting said gas along with said fossil fuel to said carbon monoxide and hydrogen.

7. The process claimed in claim 3 wherein said carbonylation is carried in effective contact with an iodine moiety.

8. The process claimed in claim 7 wherein said iodine moiety is recycled.

* * * * *

UNITED STATES PATENT OFFICE
CERTIFICATE OF CORRECTION

Patent No. 4,039,600                Dated August 2, 1977

Inventor(s) CLARENCE D. CHANG

It is certified that error appears in the above-identified patent and that said Letters Patent are hereby corrected as shown below:

Col. 2, line 42: "or 12" should be -- of twelve --

Col. 3, line 61: "U.S. patent application" should be -- U.S. application --

Col. 4, line 32: "combination" should be combinations"

Col. 4, line 49: "exchange" should be -- exchanged --

Col. 5, line 1 : "Conference or" should be -- Conference on --

Col. 7, line 48: "$C_5$+" should be -- $C_5^+$ --

Col. 7, line 48: "fractions" should be -- fraction --

Col. 7, line 49: "portions" should be -- portion --

Col. 7, line 49: "$C_4$-" should be -- $C_4^-$ --

Col. 7, line 49: "fractions" should be -- fraction --

UNITED STATES PATENT OFFICE
CERTIFICATE OF CORRECTION

Patent No. 4,039,600          Dated August 2, 1977

Inventor(s) CLARENCE D. CHANG

It is certified that error appears in the above-identified patent and that said Letters Patent are hereby corrected as shown below:

Col. 7, line 50: "$C_5+$ fractions" should be -- $C_5^+$ fraction --

Col. 8, lines 4-10: Delete

Col. 8, line 45: In Claim 6, "$C_4-$" should be -- $C_4^-$ --

*Signed and Sealed this*

*Fourth* Day of *July 1978*

[SEAL]

*Attest:*

RUTH C. MASON
*Attesting Officer*

DONALD W. BANNER
*Commissioner of Patents and Trademarks*